United States Patent [19]
Swain et al.

[11] Patent Number: 5,910,105
[45] Date of Patent: Jun. 8, 1999

[54] CONTROL HANDLE FOR AN ENDOSCOPE

[75] Inventors: Paul Swain, London, United Kingdom; Jeffrey Kapec, Westport, Conn.; Kazuna Tanaka, Cos Cob, Conn.; Feng Gong, London, United Kingdom; Geoffrey John Brown, London, United Kingdom; Gerry Ouellette, Framingham, Mass.; William M. Tennant, Jr., Nashua, N.H.

[73] Assignees: C.R. Bard, Inc., Murray Hill, N.J.; University College London, London, United Kingdom

[21] Appl. No.: 08/843,229

[22] Filed: Apr. 14, 1997

[51] Int. Cl.⁶ ............................................ A61B 1/04
[52] U.S. Cl. ........................... 600/131; 606/139; 600/104
[58] Field of Search ..................................... 600/104, 106, 600/107, 114, 123, 144, 131, 146; 606/139, 140, 141, 142, 143, 144, 145, 146, 147, 148, 149, 150

[56] References Cited

U.S. PATENT DOCUMENTS

| | | |
|---|---|---|
| 487,304 | 12/1892 | Todd . |
| 831,945 | 9/1906 | Gonyea . |
| 1,059,631 | 4/1913 | Popovics . |
| 3,013,559 | 12/1961 | Thomas . |
| 3,470,834 | 10/1969 | Bone . |
| 4,160,453 | 7/1979 | Miller . |
| 4,592,341 | 6/1986 | Omagari et al. . |
| 4,648,402 | 3/1987 | Santos . |
| 4,889,118 | 12/1989 | Schwiegerling . |
| 4,958,625 | 9/1990 | Bates et al. . |
| 5,129,912 | 7/1992 | Noda et al. . |
| 5,203,863 | 4/1993 | Bidoia . |
| 5,242,459 | 9/1993 | Bueina . |
| 5,254,126 | 10/1993 | Filipi et al. . |
| 5,281,237 | 1/1994 | Gimpelson . |
| 5,304,184 | 4/1994 | Hathaway et al. . |
| 5,318,578 | 6/1994 | Hasson . |
| 5,354,298 | 10/1994 | Lee et al. . |
| 5,364,409 | 11/1994 | Kuwabara et al. . |
| 5,364,410 | 11/1994 | Failla et al. . |
| 5,368,601 | 11/1994 | Sauer et al. . |
| 5,501,690 | 3/1996 | Measamer et al. . |
| 5,540,704 | 7/1996 | Gordon et al. . |
| 5,549,617 | 8/1996 | Green et al. . |
| 5,549,633 | 8/1996 | Evans et al. ............................ 606/139 |
| 5,564,615 | 10/1996 | Bishop et al. . |
| 5,575,800 | 11/1996 | Gordon . |
| 5,578,044 | 11/1996 | Gordon et al. . |
| 5,601,533 | 2/1997 | Hancke et al. . |
| 5,601,571 | 2/1997 | Moss . |
| 5,665,096 | 9/1997 | Yoon . |

FOREIGN PATENT DOCUMENTS

| | | |
|---|---|---|
| WO 92 04870 | 4/1992 | WIPO . |
| WO 930874 | 5/1993 | WIPO . |
| WO 94 08642 | 4/1994 | WIPO . |
| WO 95 25468 | 9/1995 | WIPO . |
| WO 9620649 | 7/1996 | WIPO . |

Primary Examiner—Beverly M. Flanagan
Attorney, Agent, or Firm—Arthur Z. Bookstein; John F. Perullo

[57] ABSTRACT

A handle is provided for attachment to a medical endoscope for advancing instrumentalities through the instrument channel of the endoscope. The handle is adapted for use with instrumentalities requiring multiple longitudinal strokes to be performed in a predetermined sequence. A detent mechanism is provided to assure that a first stroke is completed before the next succeeding stroke begins. The invention as disclosed is used to operate an endoscopic sewing machine.

23 Claims, 9 Drawing Sheets

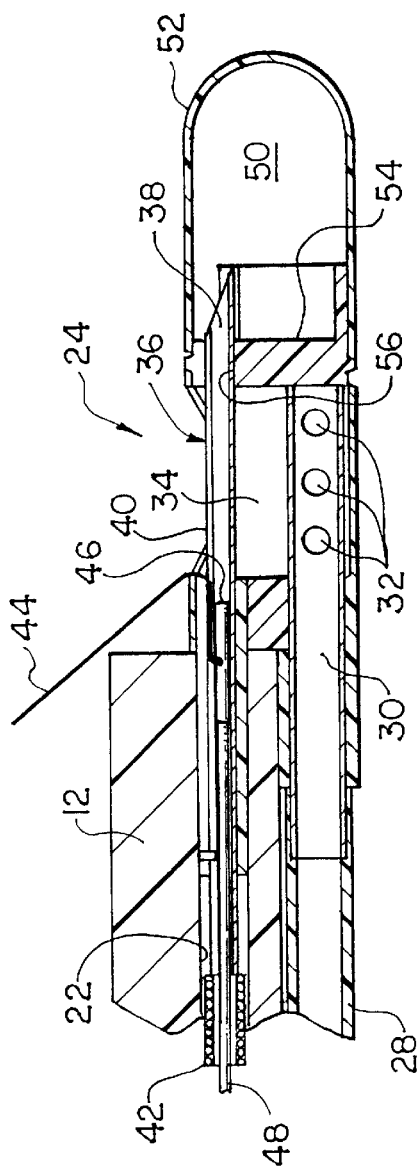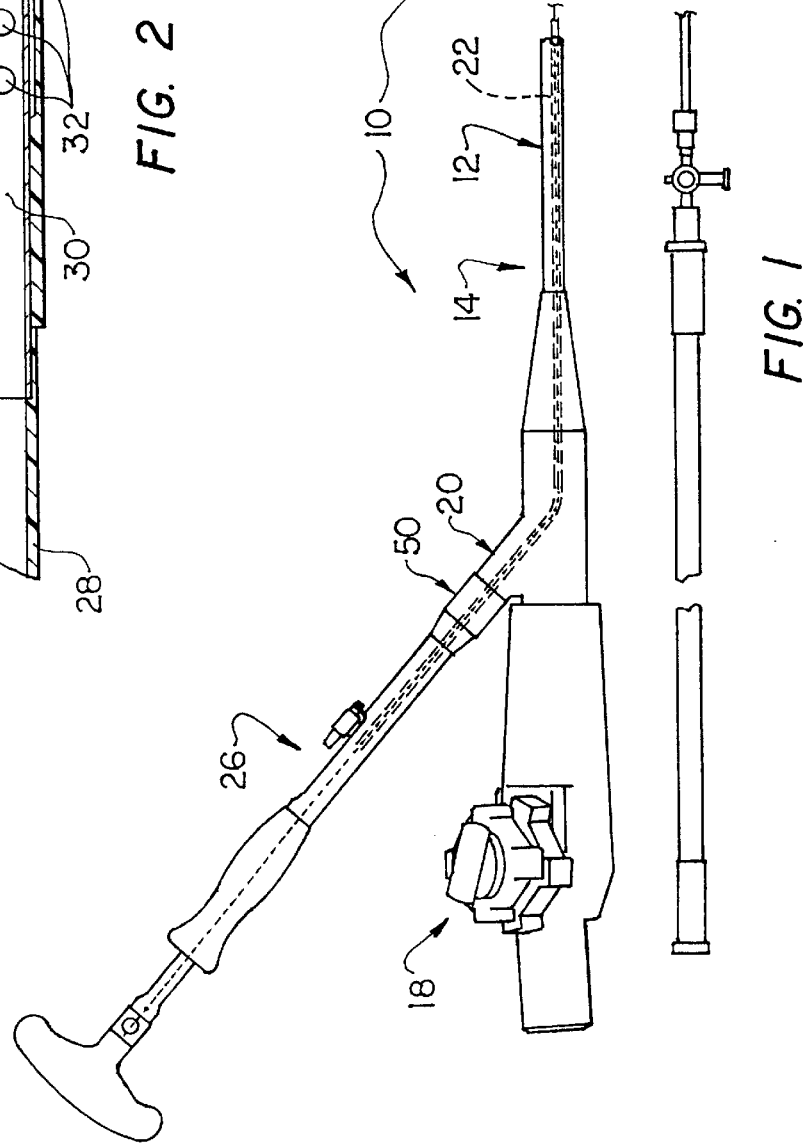

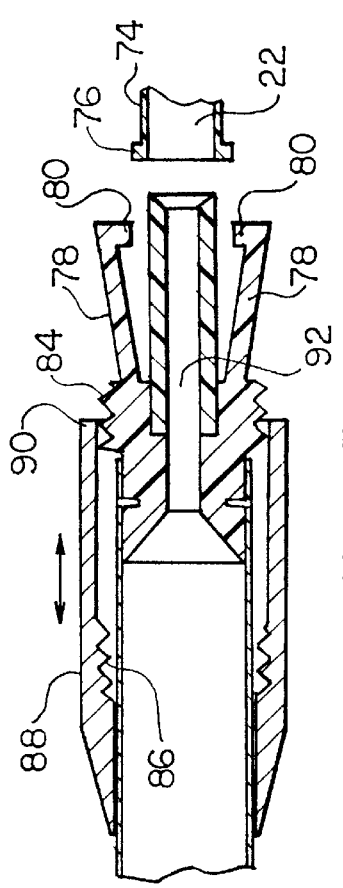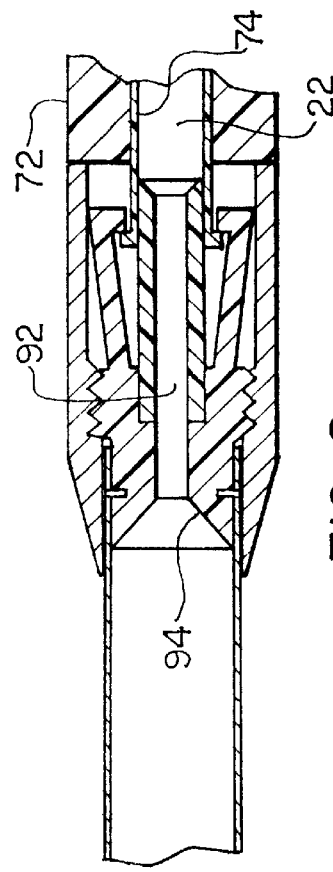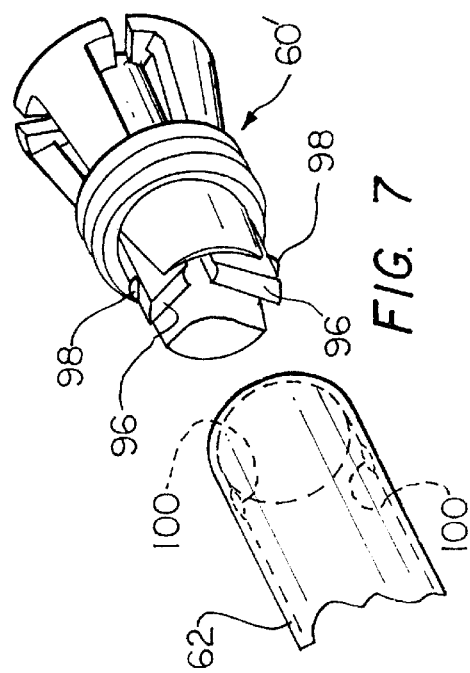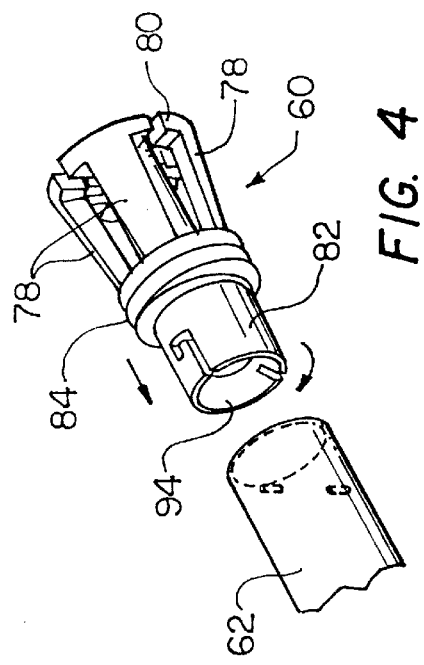

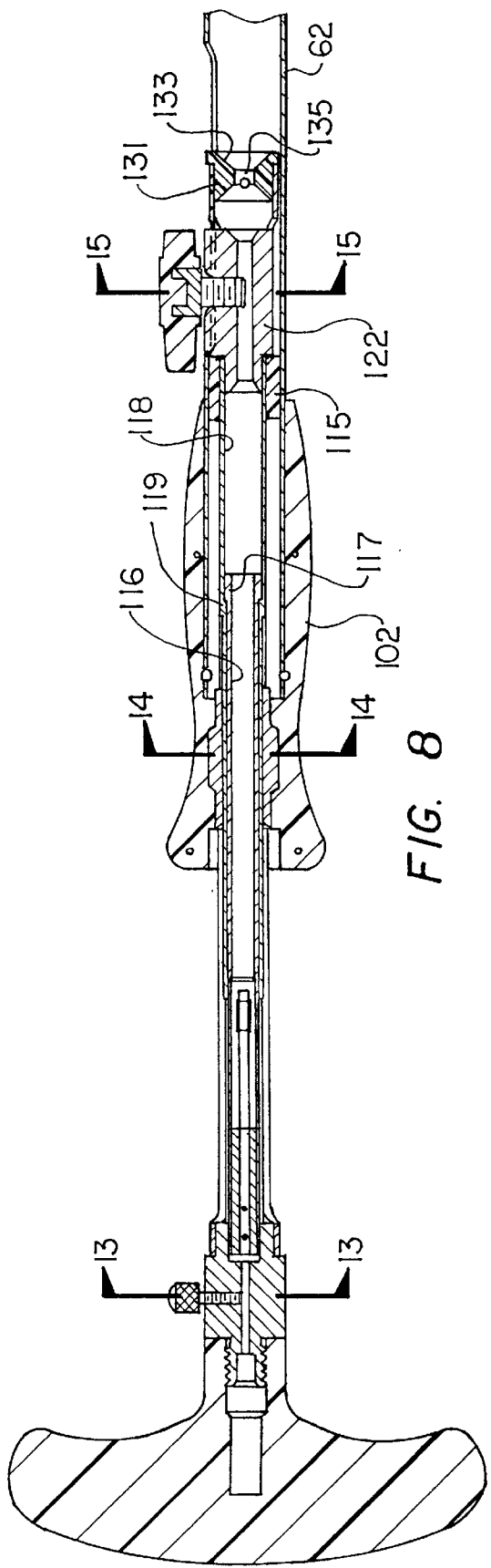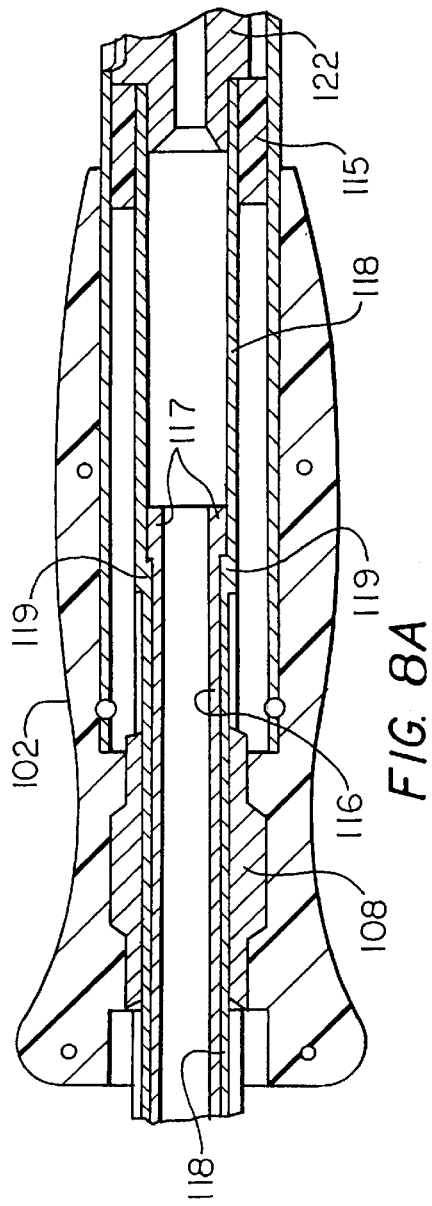

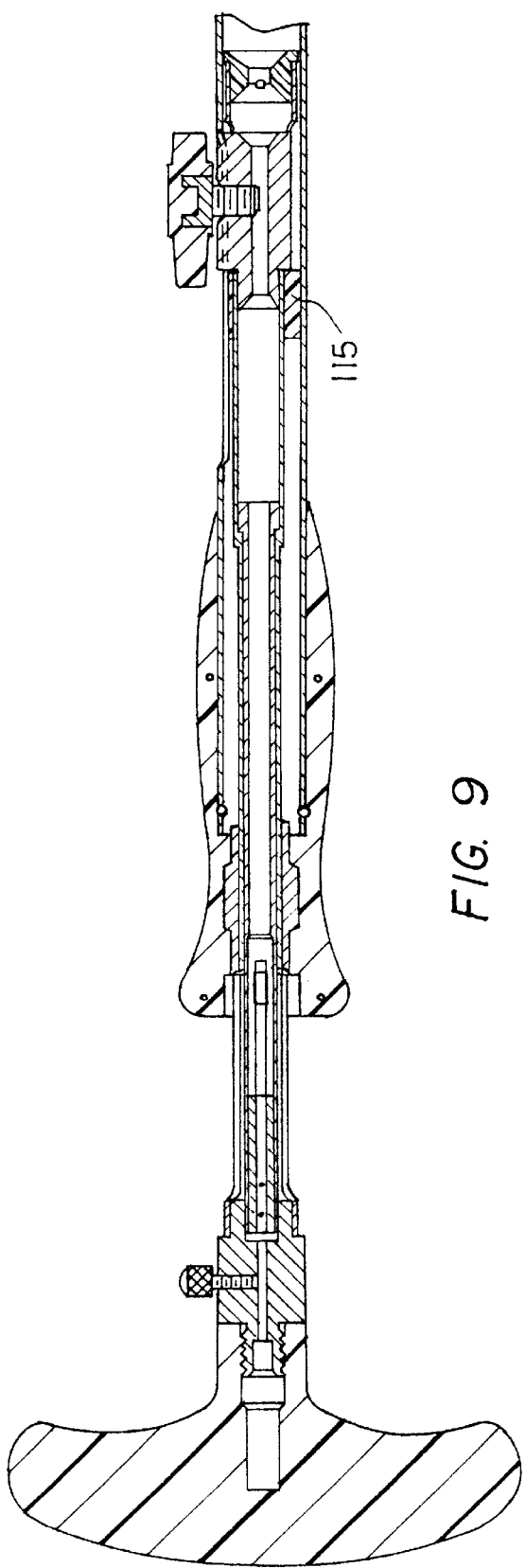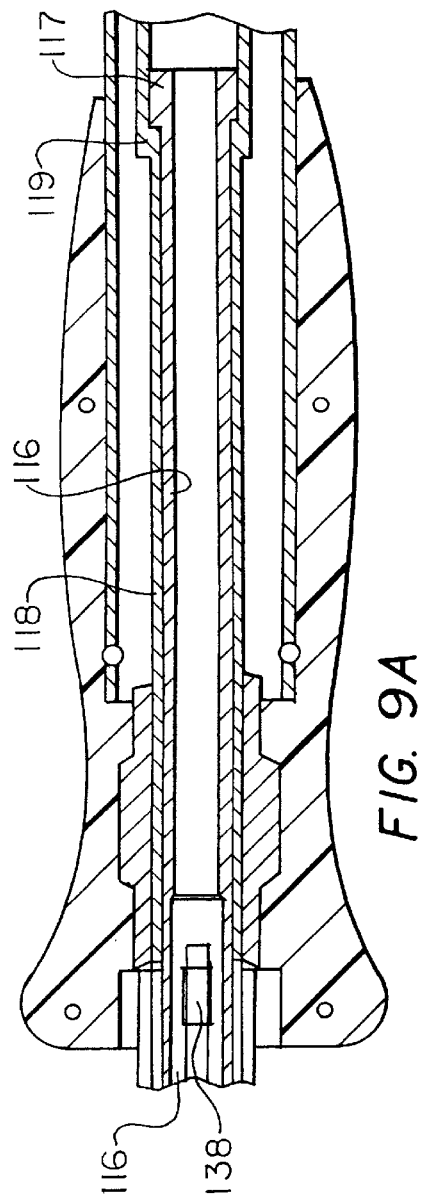
FIG. 9
FIG. 9A

CONTROL HANDLE FOR AN ENDOSCOPE

FIELD OF THE INVENTION

This invention relates to a control handle for use with a medical endoscope by which another device at the opposite end of the endoscope can be controlled through a channel of the endoscope.

BACKGROUND OF THE INVENTION

Endoscopic surgery provides many advantages over open surgery. The endoscopic procedure typically is less traumatic, can be expected to take less time and may result in a significantly shorter recuperation. The endoscope may be inserted into the patient through a natural body orifice, for example, by inserting an endoscope through the patient's mouth, through the esophagus and into the stomach. The endoscope typically has a channel through which slender instruments (e.g., cutters, biopsy forceps) can be passed to locate the distal end (inside the patient) of the instrument at the intended surgical site. The endoscope typically includes optical fiber bundles arranged to permit the physician to illuminate and view the surgical site within the patient's body. The proximal end (outside the patient) of the instrument typically is provided with controls by which the instrument can be operated to perform its intended function at the distal end.

Among the instruments adapted for endoscopic surgical use are sewing devices described in International Application No. PCT/GB95/00652. The devices are attachable to the distal end of an endoscope and are constructed to pass a suture through tissue so that the ends of the suture can be tied. The sewing devices include an arrangement by which the tissue to be sutured is drawn, by suction, into a cavity of the sewing device and, while so held, the tissue is pierced by a needle that traverses the cavity, carrying the suture through the tissue. The device includes associated mechanisms that function to separate the suture from the needle so that when the needle is withdrawn, the suture remains passed through the tissue. The ends of the suture then may be knotted with endoscopically placeable knotting instruments.

The present invention is directed to a control device, connectible to the proximal end of the endoscope and to proximally extending longitudinally moveable control elements of the sewing machine to facilitate operation of the sewing machine. One of the control elements is an elongate hollow shaft that terminates, at its distal end, in a slotted needle that pierces the tissue. The needle is adapted to carry a retention tag that is attached to one end of the suture, the suture extending out of the needle through the longitudinal slot in the needle. After the needle has been passed through the tissue, the retention tag is driven through the needle and is ejected from the distal tip of the needle by a longitudinally movable ejection wire extending through the needle shaft and needle. The ejected retention tag carries the suture with it. The sewing device includes an arrangement for capturing the retainer tag so that the end of the suture that has been passed through the tissue can be withdrawn proximally from the patient, together with the endoscope and attached sewing machine. The physician then has both ends of the suture proximally exposed to enable the suture thread to be manipulated to knot the suture at the surgical site.

SUMMARY OF THE INVENTION

The present invention relates to a control handle that is detachably connectible to the proximal end of a flexible or rigid endoscope and has several telescoping components that may be sequentially operated, first to pass the needle through the tissue and then eject the retainer tag and attached suture end from the distal end of the needle. To that end, the control handle includes first and second longitudinally moveable slides, one of which is connectible to the proximally extending end of a tubular needle shaft and another of which is attachable to the proximally extending end of an ejector wire that is slidably movable through the needle shaft and needle. The distal end of the handle is detachably connectible to the biopsy fitting that typically is disposed at the proximal end of the endoscope.

The first and second slides are arranged to define a pair of sequential strokes, the first of which advances the needle and the ejector wire in unison. The second stroke advances the ejector wire within and relative to the needle while the needle is held in place. In the first stroke, the needle is passed through the tissue and in the second stroke the retainer tag and the end of the suture to which it is connected are advanced through the needle (and, therefore, through the tissue) and are ejected from the tip of the needle into a retention chamber of the sewing device. A detent arrangement is associated between the first and second slides to assure that the ejector wire cannot be advanced relative to the needle until the needle has been advanced fully to the end of its tissue piercing stroke. Because the sliding components of the handle surround and support the distal ends of the needle shaft and ejector wire, greater axial force may be applied without causing buckling of the wire or shaft. The increased pushing force applied to the control shaft and pusher wire facilitates tissue penetration during suturing.

In another aspect of the invention, the control handle includes a connector by which the handle can be detachably connected to the biopsy fitting of the endoscope. The connector has a readily interchangeable element to enable the device to be matched to the specific configuration of the biopsy fitting of any of a variety of commercially available endoscopes.

It is among the general objects of the invention to provide a control handle mountable to the proximal end of an endoscope for sequentially controlling implements located at the distal end of the endoscope.

Another object of the invention is to provide a control handle of the type described that is adaptable to be mounted on a range of endoscopes having different connection fittings.

A further object of the invention is to provide a control handle for an endoscope for controlling the sequential functioning of a sewing device mounted to the distal end of the endoscope.

Another object of the invention is to provide a control handle mountable to the proximal end of an endoscope that is advanceable to sequential positions to control operation of a device at the distal end of the endoscope in a predetermined sequence.

Another object of the invention is to provide a control handle of the type described in which a detent is provided between movable members of the control handle to preclude advancement of one component of the handle before the advancement of another handle component has been completed.

DESCRIPTION OF THE DRAWINGS

The foregoing and other objects and advantages of the invention will be appreciated more fully from the following further description thereof, with reference to the accompanying drawings wherein:

FIG. 1 is a somewhat diagrammatic, fragmented illustration of an endoscope with a sewing device attached to its distal end and a control handle of the invention attached to the biopsy fitting at the proximal end of the endoscope;

FIG. 2 is an enlarged, somewhat diagrammatic, sectional illustration of the endoscopic sewing device;

FIG. 4 is an illustration of one embodiment of a collet for connecting the handle to the biopsy fitting of the endoscope;

FIG. 5 is a sectional illustration of the distal end of the handle with the collet in readiness to engage the proximal end of the biopsy fitting of the endoscope;

FIG. 6 is an illustration similar to FIG. 5 after the handle has been connected to the biopsy fitting of the endoscope;

FIG. 7 is an illustration of another embodiment of an interchangeable collet;

FIG. 8 is a longitudinal sectional illustration of the handle in its fully retracted position in readiness to be advanced in its first stroke;

FIG. 8A is an enlarged sectional illustration of the hand grip region of the device when in the configuration show in FIG. 8;

FIG. 9 is a longitudinal sectional illustration of the control handle in its intermediate position between completion of the first stroke and before initiation of the second stroke;

FIG. 9A is an enlarged sectional illustration of the region of the hand grip when the device is in the configuration shown in FIG. 9;

DESCRIPTION OF THE ILLUSTRATIVE EMBODIMENTS

Figure 3:
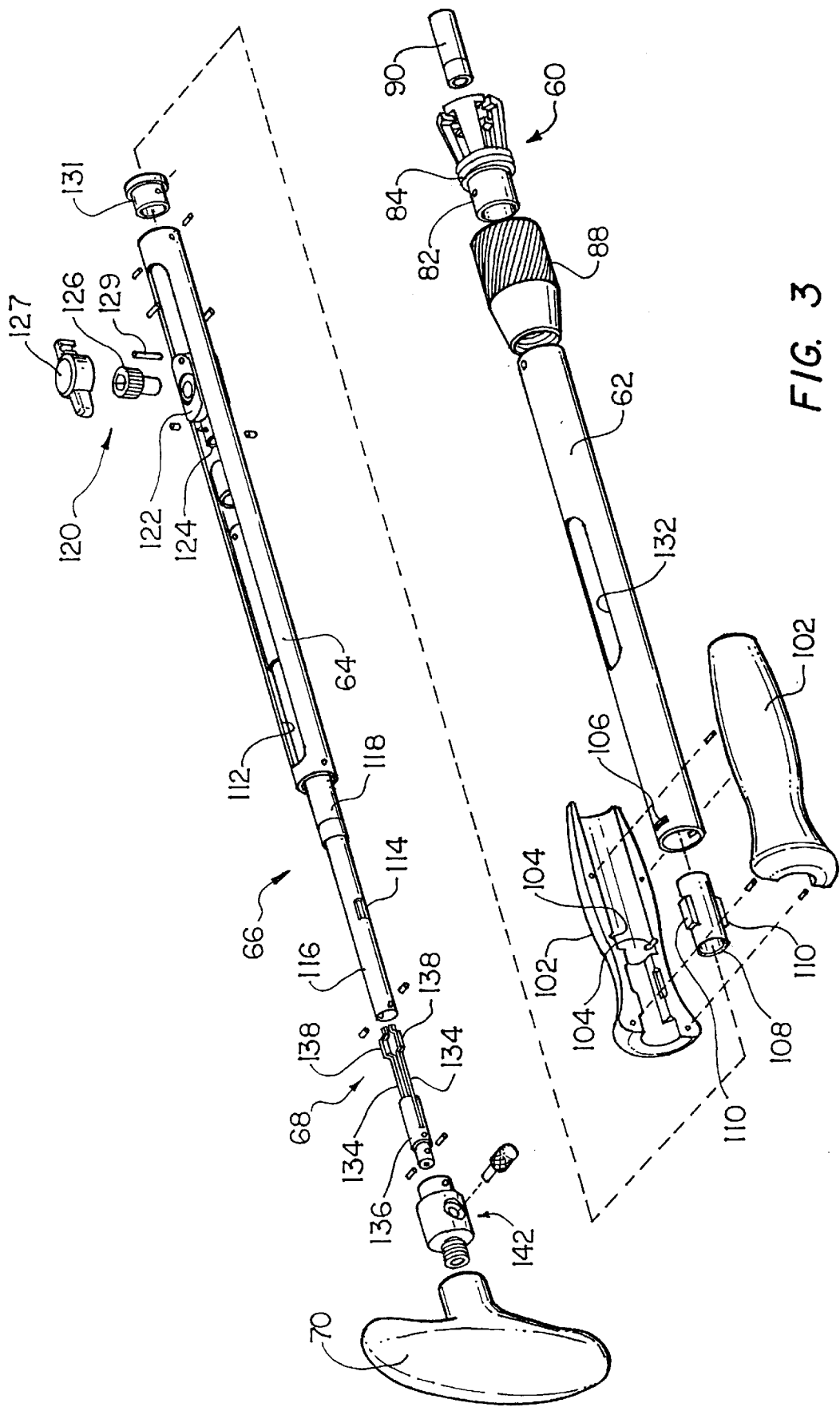
FIG. 3 is an exploded illustration of the handle.
Figure 3A:
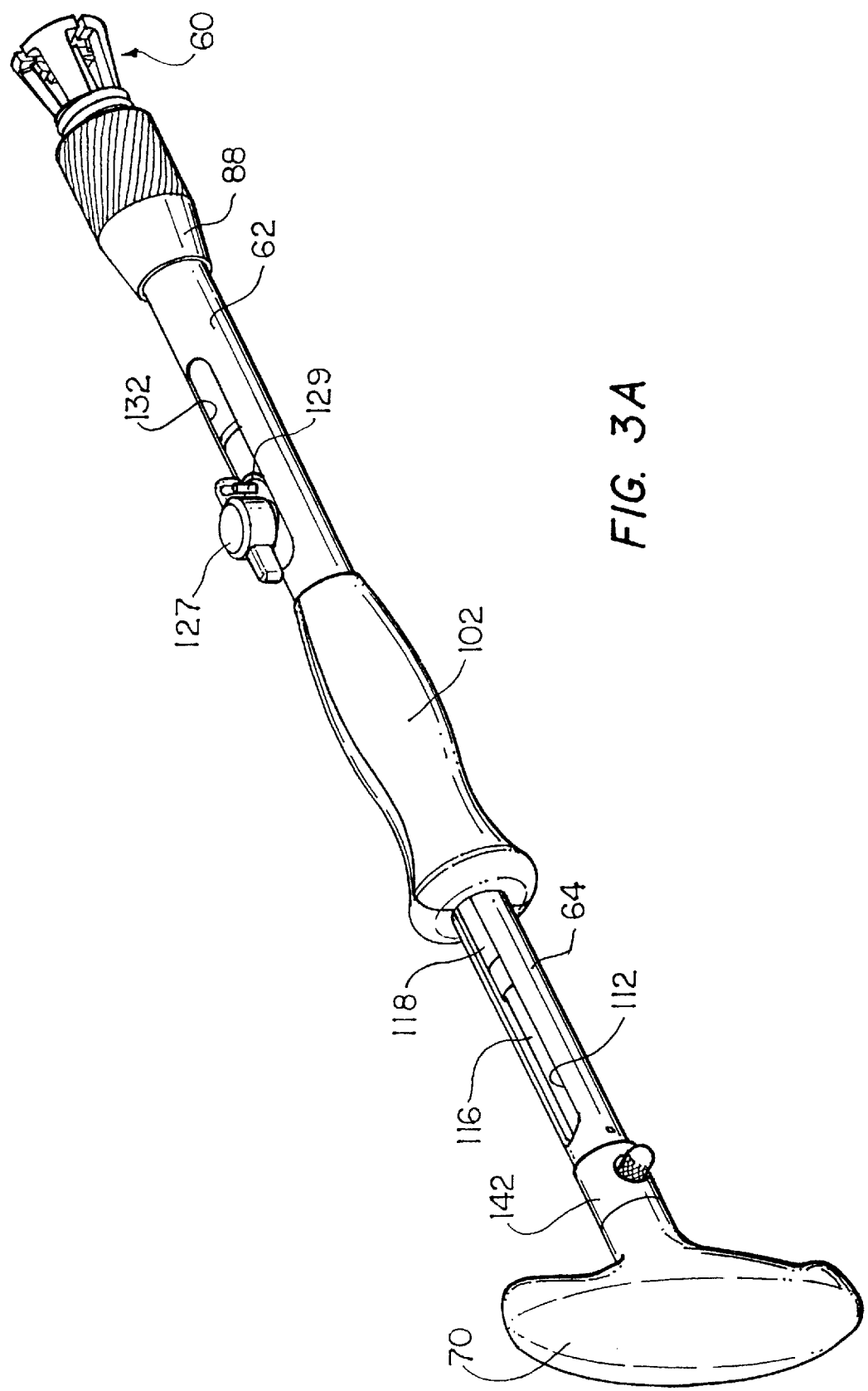
FIG. 3A is an illustration of the assembled handle.

FIG. 1 illustrates a typical endoscope that may be used in connection with stomach procedures including an elongate flexible shaft 12 having a proximal end 14 and a distal end 16. The proximal end of the endoscope 10 includes fittings and controls to operate the endoscope, including control knobs 18 and a biopsy fitting 20. The fitting 20 provides access to a biopsy channel 22 that extends through the shaft 12 and terminates at a distal opening at the distal end of the shaft 12. FIG. 1 also shows the endoscope as having a sewing device 24 attached to its distal end and a control handle 26 attached to the biopsy fitting 20 at the proximal end of the endoscope 10.

FIG. 2 illustrates a sewing device 24 attached to the distal end of the shaft 12 of the endoscope. The sewing device 24 includes a proximally extending suction tube 30 that connects to a tube 28 that extends along and outside of the endoscope. The proximal end of the tube 28 is connectible to a source of suction. The suction tube 30 defines a flow path and has a plurality of openings 32 that communicate with a transversely open cavity 34 formed in the sewing device. As described in more detail in the aforementioned International application, the disclosure of which is incorporated herein in its entirety by reference, suction is applied to the cavity 34 to draw a fold of tissue into the cavity so that a needle can be driven through the tissue fold. The sewing machine includes a hollow, slotted needle 36 having an inner lumen 38 and a longitudinal slot 40 that extends to the tip of the needle. The proximal end of the needle is attached to the distal end of an elongate tubular shaft 42 that preferably is formed from a flexible helical coil encased by a lubricious jacket, such as PTFE, along its length. The inner lumen 38 of the needle and the inner lumen defined by the elongate tubular shaft 42 communicate with each other to define a continuous lumen. The coiled tubular shaft 42 extends proximally within the biopsy channel 22 of the endoscope shaft 12, passing through the biopsy fitting 20 where it is connected to the control handle 26. As described in further detail below, the first stroke of the control handle serves to drive the shaft 42 and needle 36 in a distal direction, in which the needle 36 passes through the cavity 34 as shown in FIG. 2.

FIG. 2 shows the sewing device in a configuration in which the needle has been passed through the tissue (not shown). When the device is set up before insertion into the patient, it is loaded with a suture 44, an end of which is secured to a retention tag 46. As shown in FIG. 2, the tag 46 is slidably contained within the lumen 38 of the needle 36 with the suture 44 extending out of the side of the needle through the needle slot 40. The sewing device also includes an ejection wire 48 that is received slidably through the contiguous lumens of the shaft 42 and needle 36. The proximal end of the ejection wire 48 extends into the control handle and is connected to the handle so that it can be advanced distally relative to the needle with the second stroke of the handle, to eject the tag from the needle and into a tag retention chamber 50, described below.

The chamber 50 is defined in part by a hollow end cap 52 and an internal wall 54 that separates the chamber 50 from the tissue cavity 34. The wall 54 is formed to define an aperture 56 in alignment with the needle 36 so that when the needle is advanced through the tissue it can project through the aperture and into the chamber 50. The ejector wire 48 then can be advanced distally, relative to the needle, to drive the retention tag 46 out of the needle 36 and into the chamber 50, carrying the end of the suture with it. The suture passes through the slot 40 as the retention tag 46 is advanced. When the needle is retracted and the suction is terminated to release the tissue, the suture will have been passed through the tissue and the retention tag will be captured within the chamber 50. The end of the suture 46 preferably is attached to the middle of the retention tag so that the suture and tag will assume a T-shape that cannot pass through the aperture 56. The endoscope, with sewing device attached, then can be withdrawn from the patient, drawing the tag end of the suture 44 proximally outside of the patient. The original free end and the withdrawn free end of the suture then can be knotted and the knot advanced into the patient as described in International Patent Application Publication No. PCT/GB93/01859.

The structure and functional positions of the control handle 26 are shown in FIGS. 3 and 8–15. The control handle 26 includes a handle connector, indicated generally at 58, at the distal end of the handle assembly. The handle connector 58 includes an interchangeable connector element, shown in the illustrative embodiment as a collet 60. The collet 60 is adapted to connect with mating components of the biopsy fitting 20 of the endoscope. By changing the collet for a differently configured collet or other connector, the control handle 26 may be used with a range of commercially available endoscopes.

The control handle 26 includes several slides, shown in the form of telescoping tubes including an outer tubular housing 62, an outer tubular carrier slide 64 slidable within the tubular housing 62, and a telescopically collapsible pusher slide assembly, indicated generally at 66. The pusher tube assembly 66 includes a detent mechanism 68, described below, that defines the transition from the needle advancing portion of the stroke to the ejection portion of the stroke. The detent provides tactile feedback for the physician to signal that the needle piercing stroke has been completed. The proximal ends of the outer carrier slide 64, pusher tube assembly 66 and detent mechanism 68 are secured together and to a handle 70. As described in further detail below, the proximal end of the elongate tubular shaft 42 to which the needle 36 is attached, is connectible to the distal end of the pusher tube assembly 66. The ejection wire 48 extends within and proximally beyond the proximal end of the shaft 42. The proximal end of the ejection wire 48 is connectible to the device in the region of the handle 70 so that it can move in unison with the handle. As will be described in further detail, during the first portion of the stroke, the handle 70, pusher tube assembly 66 and all components carried thereby, advance in unison to drive the needle 36 through the tissue, the ejector wire 48 being carried in unison within the needle 36 and shaft 42. At that time, the detent mechanism 68 provides an increased resistance to further advancement, thereby signaling to the physician that the needle piercing stroke has been completed. Further advancement of the handle overcomes the detent mechanism 68 and enables the pusher tube assembly 66 to collapse telescopically, thereby enabling the ejector wire to be advanced to eject the retention tag 46 and suture 44 from the needle into the chamber 50. In addition to controlling movement, the control handle serves to support the proximal ends of the ejection wire 48 and shaft 42 along their longitudinal axis. Therefore, the axial loads that may be placed upon these elongate members without causing buckling, is greater than if the members were manipulated without the control handle. The increased axial loading permitted by using the control handle not only facilitates tissue penetration by the needle, but also helps overcome additional friction that may be encountered as the control shaft 42 negotiates curves in a flexible endoscope.

FIGS. 4–6 illustrate, in further detail, the connector assembly 58 by which the control handle 26 is detachably connected to the biopsy fitting 20 of the endoscope. FIGS. 5 and 6 illustrate, diagrammatically, the configuration of a portion of the biopsy fitting 20. The biopsy fitting may include the fitting housing 72 (FIG. 6) and a tubular extension 74 having a flange 76 surrounding the proximal end of the extension 74. The tubular extension 74 defines the proximal end of the biopsy channel 22. The collet 60 may be molded from a flexible, high strength plastic, such as Delrin, to include a plurality of distally diverging, flexible fingers 78, each having a radially inwardly extending projection 80. The proximal end 82 of the collet 60 is connectible to the distal end of the outer tubular housing 62, as by a bayonet connection shown in FIG. 4. The collet 60 also includes external threads 84 adapted to be engaged by internal threads 86 on a collet nut 88. The collet nut 88 is rotatably and slidably mounted along the exterior of the distal end of the outer housing 62. The internal threads 86 are located so that they will engage the external threads 84 after the distal end 90 of the collet nut has engage the fingers 78 sufficiently to draw them inwardly. As shown in FIG. 6, when the collet 60 and tubular extension 74 are securely engaged, the projections 80 will engage the flange 76 to provide a secure docking between the two. The collet 60 may be provided with a docking tube 90 that is receivable in the biopsy lumen 22 of the tubular extension 74. The docking tube has a through lumen 92 that continues proximally through the collet and terminates at a funnel-shaped opening 94 at the proximal end of the collet 60.

FIG. 7 shows a modified connection between the proximal end of the collet 60' and the distal end of the housing 62. In this embodiment, the proximal end of the collet may be formed to include a pair of opposed fingers 96 that have the ability to flex inwardly and resiliently. The outer faces of the fingers may be provided with bumps 98 adapted to engage complementary sockets 100 formed on the inner surface of the distal end of the outer housing 62. The bumps 98 and sockets 100 cooperate to provide a secure, yet detachable, snap-fit connection. It should be understood that although the illustrative embodiment is disclosed in connection with a collet, other interchangeable connectors may be employed depending on the configuration of the biopsy fitting 20 of a particular manufacturer.

The outer housing 62 has a hand grip 102 attached to its proximal end. The hand grip 102 may be formed in mating halves (FIG. 3) provided with slots 104 adapted to receive projections 106 on the proximal end of the housing 62. A tubular bushing 108 is captured between the mating halves of the hand grip 102 and includes radial projections 110 received in complementary sockets in the hand grip halves to securely retain the bushing 108 in place. The arrangement of the hand grip 102 and handle 70 facilitates two-handed operation of device. That enables the endoscopist to apply a greater driving force than might be obtained with a device adapted for one handed operation, should such additional force be desired. Other hand grip configurations may be used, as desired, such as hand grip employing integral fingers rings (not shown) to facilitate one handed actuation.

Figure 14:
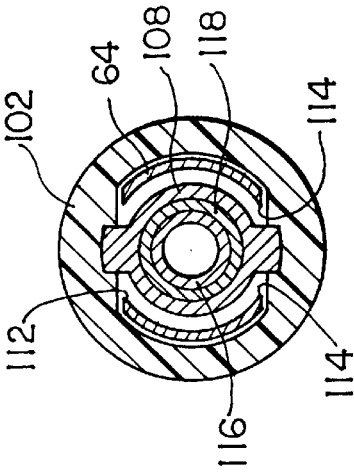
Figure 13:
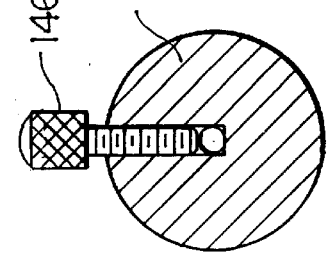
Figure 16:
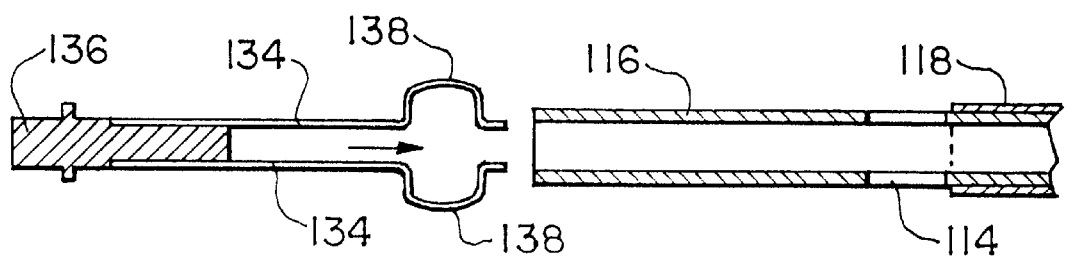

The outer slide carrier slide 64 is slidably and telescopically contained within the outer housing 62 and is provided with upper and lower longitudinal slots 112, 114 (FIG. 14). The device is assembled so that the radial projections 110 of the bushing 108 protrude radially outwardly through the longitudinal slots 112,114. When the device is assembled, the engagement of the ends of the slots 112,114 with the projections 106 define the proximal and distal extremities of longitudinal motion of the outer carrier slide 64 within the housing 62. Consequently, the outer carrier slide 64 moves throughout the full range of motion of the device, including both strokes of the device.

Figure 10:
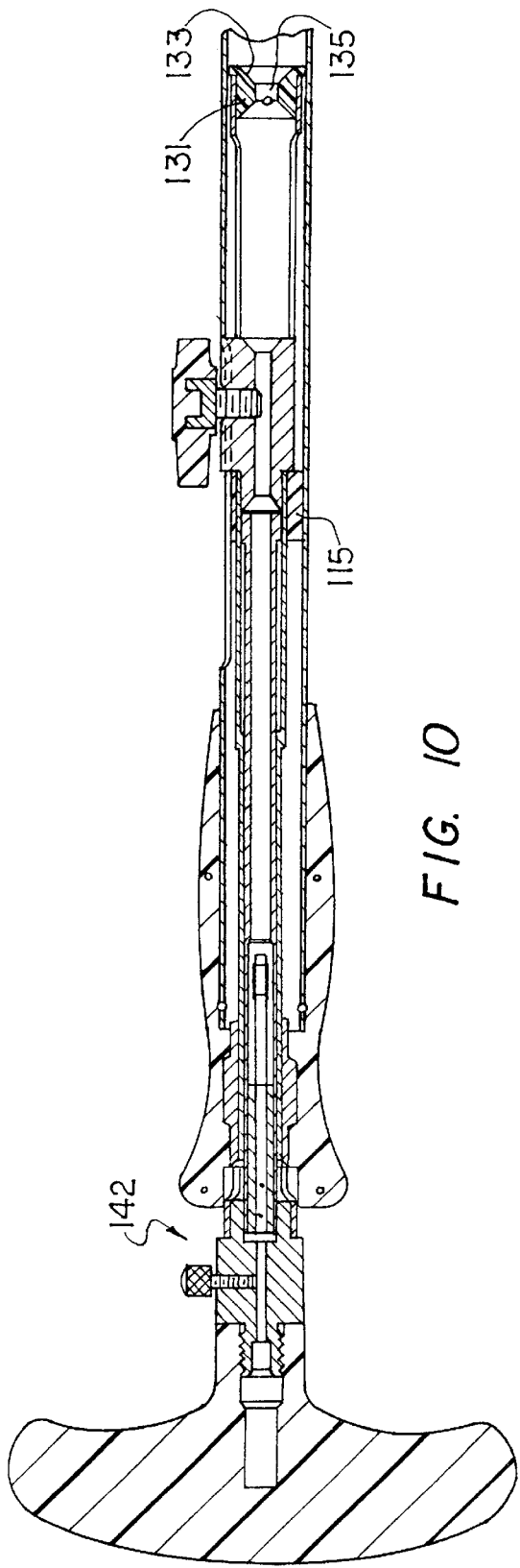
FIG. 10 is a longitudinal sectional illustration of the control handle in its fully forward configuration after completion of the second stroke.
Figure 10A:
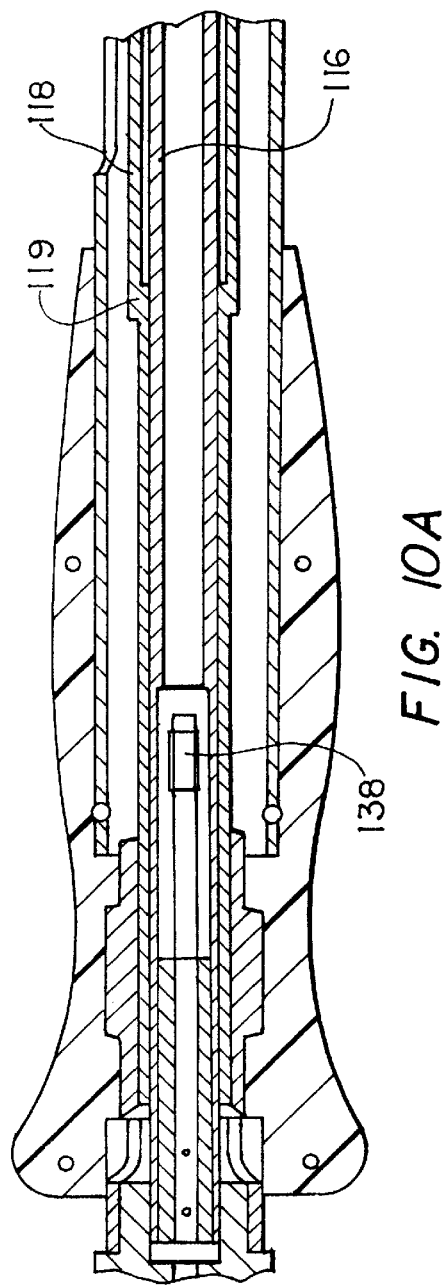
FIG. 10A is an enlarged sectional illustration of the hand grip region of the device when in the configuration shown in FIG. 10.
Figure 12:
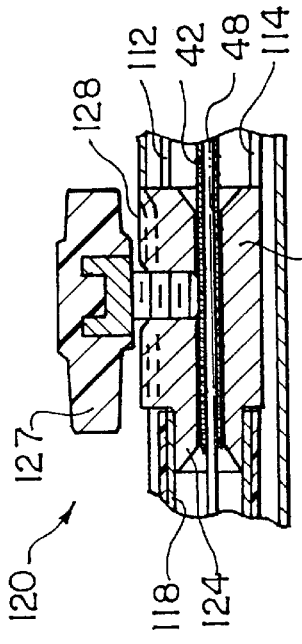
FIG. 12 is an enlarged sectional illustration of the region of the control handle to which the proximal end of the needle assembly is attached.
Figure 11:
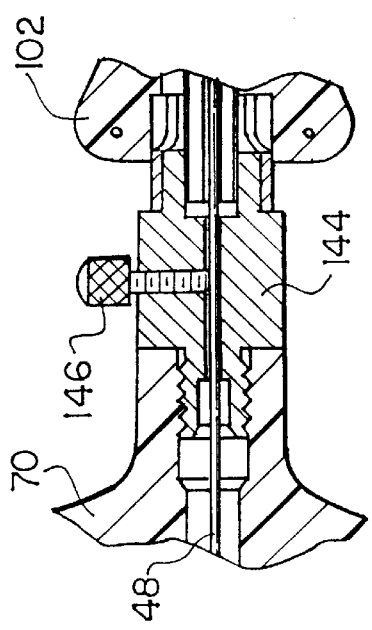
FIG. 11 is an enlarged cross-sectional illustration of the region where the proximal end of the ejection wire is attached to the control handle.
Figure 15:
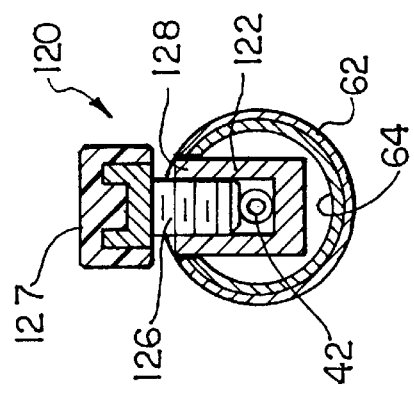
FIGS. 13–15 are sequential, diagrammatic, cross-sectional illustrations of the detent mechanism in various stages of operation.

The pusher tube assembly 66 is mounted for longitudinal slidable movement within the outer carrier slide 64. The pusher tube assembly 66 includes inner and outer telescoping tubes 116, 118. The outer tube 118 is slidably received through the bushing 108. The inner tube 116 is slidably received within the outer tube 118. The distal end of the outer tube is secured to a clamping mechanism, indicated generally at 120, and illustrated in enlarged detail in FIGS. 12 and 15. A low friction plastic bushing 115 may be disposed about the end region of the outer tube 118. The clamping mechanism is adapted to receive the proximal end of the elongate tubular shaft 42 to functionally secure it to the distal end of the outer tube 118. The longitudinal movement of the clamping mechanism 120 determines the length of the stroke of the needle 36 at the distal end of the shaft 42. The limit of proximal movement of the inner tube 116 relative to the outer tube is defined by engagement of shoulders 117,119 formed internally of the tubes 116,118, respectively, as shown in FIGS. 8A, 9A and 10A.

The clamping mechanism 120 includes a block-like member 122 having a longitudinal lumen and a projection 124 at its proximal end that is received within and secured to the distal end of the outer tube 118. The proximal and distal ends of the lumen through the block 122 may be funnel-shaped (FIG. 12) to facilitate entry of the proximal end of the shaft 42 into the block 122. A clamping screw 126 is threaded transversely and downwardly into the block and can be tightened to securely clamp the proximal end of the shaft 42 to the block 122 and, therefore, functionally to the end of the outer tube 118 of the pusher tube assembly. Approximately one centimeter of the PTFE jacket may be stripped away from shaft 42 at its proximal end to enhance the frictional contact of clamping screw 126 against the stainless steel coil shaft. Means are provided to limit the extent to which the clamping screw 126 can be tightened in order to avoid damaging the engaged portion of the shaft 42. To that end, a knob 127 may be attached to the end of the screw. The block 122 may be provided with an upwardly extending pin 128 that serves as a stop engageable by a portion of the knob 127 to prevent overtightening of the screw. The upper end 128 of the block 122 protrudes through upper slots 112 of the outer carrier slide 64 beyond the outer carrier slide 64 and into a relatively short slot 132 formed along the upper surface of the outer housing 62. The proximal and distal ends of the slot 132 define the limits of longitudinal movement of the clamp assembly 120 and, therefore, of the shaft 42 and needle 36. When the upper end 128 of the block 122 engages the distal end of the slot 132, the forward movement of the shaft 42 and needle is terminated, thereby defining the end of the needle piercing stroke of the device. The distal end of the outer carrier slide 64 may be provided with a guide 131 having a distally facing conical surface 133 that converges to an opening 135. The guide 131 serves to guide the shaft 42 when it is loaded into the handle, as described below.

Figure 17:
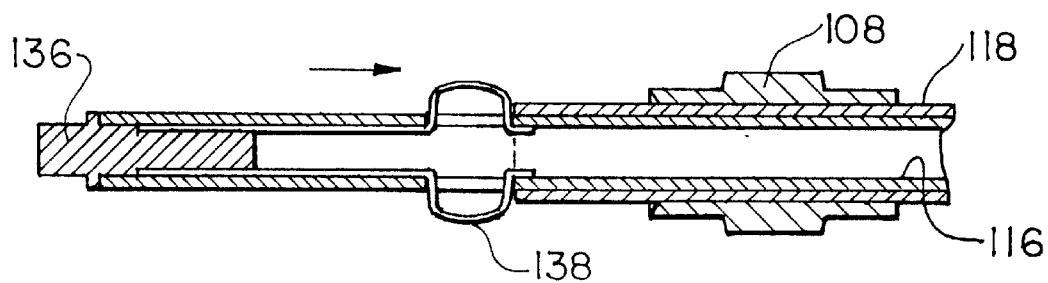

The detent mechanism 68 is illustrated in detail in FIGS. 3 and 16–18. In the illustrative embodiment, the detent mechanism 68 include a pair of longitudinally extending, transversely spaced leaf springs 134 extending longitudinally within the inner tube 116 of the pusher tube assembly 66. The proximal ends of the leaf springs 134 are secured together by a spring support 136 that is secured to the proximal end of the inner tube 116. Each leaf spring 134 includes a transversely projecting detent 138. The detents 138 project radially through a pair of transversely opposed openings 114 formed in the inner tube 116. The detents 138 extend radially a distance greater than that defined by the diameter of the outer tube 118 of the pusher tube assembly 66. The parts are dimensioned, however, so that when the leaf springs 134 flex radially inwardly together, the outer extremities of the detent 138 can be received within the lumen of the outer tube 118 (FIG. 17). When the inner and outer tubes are configured as illustrated in FIGS. 9 and 17, with the detents projecting radially outwardly and in engagement with the proximal end of the outer tube 118, the detents 138 will present tactile resistance to further advancement of the handle 70 relative to the housing 62. The leaf springs 134 will yield after a distinct additional force is applied to the handle 70 to cause the springs 134 to draw inwardly and permit the inner tube 116 to continue to advance distally relative to the outer tube 118, in telescopic fashion. The engagement of the detents 138 with the proximal end of the outer tube 118 indicates the point of transition between the first, needle piercing stroke and the second, ejection wire stroke.

The ejection wire 48 extends through the flexible tubular shaft 42, proximally beyond the clamp 120 to a wire clamp 142 adjacent the handle 70. As illustrated in enlarged detail in FIG. 11, the wire clamp 142 includes a clamping block 144 that is secured to the proximal extremity of the outer carrier slide 64, inner tube 116 and spring support 136 to be movable as a unit. A thumb screw 146 is threaded into the block 144 to releasably, but securely, grip the proximal end of the ejection wire 48. The handle 70 may be threaded onto a proximal threaded extension integral with the block 144.

When setting up the device for use, the control handle 30 is attached to the biopsy fitting 20 at the proximal end of the endoscope. The handle 70 then may be unscrewed from the wire clamp block 144 to expose the proximal end of the wire-receptive lumen. The ejection wire 48 then is inserted through the clamp block 144, the pusher tube assembly 66, the shaft clamping mechanism 120, the lumen 92 of the collet 60 and into the biopsy channel 22. The shaft 42 to which the needle 36 is attached then is loaded through the distal opening of the biopsy channel and is advanced proximally through the biopsy channel, with the ejection wire being received within the lumen of the shaft 42. The shaft 42 is advanced until its proximal end is received in the clamping mechanism 120, at which time the clamping screw 126 is tightened. After the ejection wire 48 and shaft 42 have been loaded into the endoscope and connected to the handle, the sewing device 24 is attached to the distal end of the endoscope. The control handle should be advanced to test its full distal position in order to facilitate adjusting the clamped locations of the ejection wire and shaft to insure that the proper relative stroke lengths of the needle and ejection wire. Preferably, the shaft position should be adjusted so that the distal tip of the needle advances about five millimeters beyond the wall 54 into the chamber 50. The ejection wire then should be adjusted so that at the end of its distal stroke, it will extend about five millimeters beyond the distal tip of the needle. The clamping screws 126, 146, then can be secured in their final positions.

With the device so set-up, the retention tag 46 can be loaded into the needle 36 with the suture projecting out of the cavity 34 and running alongside the exterior of the endoscope. With the handle withdrawn to its full proximal position (FIG. 8), the endoscope then is advanced into the patient to locate the sewing device 24 at the site to be sutured. When the handle is withdrawn to its full proximal position, the detents 138 protrude through the opening 114 in the inner tube 116 and in abutment with the proximal end of the outer tube 118 (FIG. 17). Suction then is applied to draw a fold of tissue into the cavity 34 of the sewing device 24. The handle then is urged distally to advance, in unison, the outer carrier slide 64 and pusher tube assembly 66 in the first stroke. In the first stroke, the needle and ejection wire advance distally in unison without relative movement between the two. The first stroke terminates when the block 122 engages the distal end of the upper slot 112. That indicates that the needle has completed its piercing movement and has been driven through the tissue, with its tip extending into the chamber 50.

Figure 18:
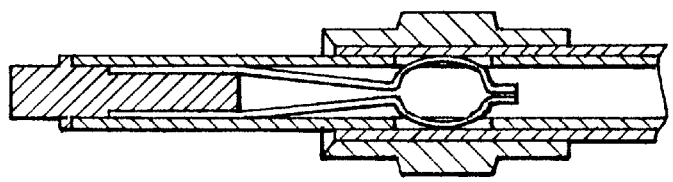

Further forward movement of the outer tube 118 thus is precluded by engagement of the block 122 at the distal end of the upper slot. In order to eject the tag from the distal end of the needle into the chamber 50, the second stroke is effected by increasing pressure on the handle to overcome the resistive force of the detent mechanism. That causes the leaf springs 134 to flex so that the detents 138 draw inwardly as shown in FIG. 18. Continued advancement of the handle thereafter drives the inner tube 116 telescopically into the outer tube 118, permitting the advancement of the ejection wire through the needle to eject the retention tag into the chamber 50. The endoscope then can be withdrawn, carrying with it the sewing device and the end of the suture retained within the chamber 50 by the retention tag. The cap of the sewing device then can be removed (or the suture can be cut). The free ends of the suture then can be knotted and the knot advanced into the patient by conventional means.

From the foregoing, it will be appreciated that the invention provides a control for serial advancement of components extending into and through the biopsy channel of an endoscope. The device provides distinct tactile response for the physician to distinctly identify the transition from one phase to the next. The device includes a convertible connector system by which it can be attached to the biopsy fitting of an endoscope of a wide range of endoscopes of different manufacturers.

It should be understood, however, that the foregoing description of the invention is intended merely to be illustrative thereof and that other modifications, embodiments and equivalents may be apparent to those skilled in the art without departing from its spirit.

Having thus described the invention, what we desire to claim and secure by Letters Patent is:

1. A control device connectable to the proximal end of an endoscope for effecting sequential advancement of longitudinally movable members through a channel of an endoscope comprising:
   an elongate frame;
   a connector at the distal end of the frame for connection to an endoscope;
   a first slide longitudinally movable with respect to the frame, the slide having a first connector for connection to a first longitudinally movable member;
   a second slide longitudinally movable in unison with and relative to the first slide;
   a second connector operatively associated with the second slide for connection to a second longitudinally movable member.

2. A control device a defined in claim 1 further comprising:
   a detent mechanism operatively associated between the first and second slides to provide a resistance to relative movement of the second slide, in a distal direction, to the first slide.

3. A control device as defined in either one of claims 1 or 2 further comprising:
   the frame having proximal and distal limit stops engageable with the first slide to limit the longitudinal stroke of the first slide.

4. A control device as defined in claim 2 further comprising:
   the frame having proximal and distal limit stops engageable with the first slide to limit the longitudinal stroke of the first slide; and
   an actuator carried by the frame and located in a position to engage the detent when the first slide is at its most distal position, to release the detent and permit relative advancement of the second slide to the first slide.

5. A control device as defined in claim 1 wherein:
   the frame comprises a tube, the first and second slides being longitudinally movable within the tube.

6. A control device as defined in claim 5 further comprising:
   the frame defining a longitudinal slot having proximal and distal ends;
   the first slide having a radially projecting member extending through the slot, engagement of the radially projecting member defining the proximal and distal extremities of the longitudinal stroke of the first slide.

7. A control device as defined in claim 6 wherein the radially projecting member comprises the first connector.

8. A control device as defined in claim 7 wherein the radially projecting member includes a clamp for releasingly clamping the first longitudinally movable member.

9. A control device as defined in claim 5 further comprising:
   an elongate carrier slidable within the frame, the first and second slides being carried by the carrier.

10. A control device as defined in claim 9 wherein the first and second slides are tubular and are telescopically arranged for slidable movement, one within the other.

11. A control device as defined in claim 10 further comprising:
    a detent associated with the first and second slides to present a yieldable resistance to their telescoping.

12. A control device as defined in claim 11 further comprising:
    a detent actuator on the frame, engageable with the detent when the first slide is in its most distal position to release the detent thereby enabling relative distal telescoping movement of the second slide relative to the first slide.

13. A control device as defined in claim 12 wherein the detent comprising:
    at least one radially projecting detent element carried by the first slide, the detent element projecting radially beyond the outer diameter of the second tube and the inner diameter of the first tube;
    the detent being resiliently biased radially outwardly.

14. A control device as defined in claim 13 wherein the detent further comprises:
    at least one leaf spring carried by the second tube and associated with the detent element to resiliently bias the detent element radially outwardly.

15. A control device as defined in claim 14 wherein the detent element is integral with the leaf spring.

16. A control device as defined in 2 wherein the second connector is located proximally of the detent.

17. A control device as defined in claim 1 wherein the frame connector includes a connector element adapted to detachably connect the frame to the endoscope, the connector element being detachably mounted to the distal end of the frame, thereby enabling the connector element to be interchanged with another connector element adapted for connection to an endoscope having different connective geometry.

18. A control device as defined in claim 17 wherein the proximal end of the connector element is attachable to the distal end of the frame by a bayonet fitting.

19. A control device as defined in claim 17 wherein the proximal end of the connector element is detachably connected to the distal end of the frame by a snap-fitting.

20. A control device as defined in claim 1 wherein the frame connector includes a collet having distally diverging fingers; and a collet nut mounted on the end of the housing and advanceable in a distal direction to constrict and clamp the collet fingers to and about a portion of the endoscope.

21. A control device as defined in claim 20 further comprising:

the connector element including a distally extending docking tube insertable into the proximal end of the endoscope channel.

22. A control control device as defined in claim 1 wherein one of the longitudinally movable members is constructed to pass through a second longitudinally movable member.

23. A control device as defined in claim 1 further comprising in combination:

an endoscope having a proximal end connected to the control device at the distal end of the frame.

* * * * *